United States Patent
Doiron et al.

[11] Patent Number: 5,978,541
[45] Date of Patent: Nov. 2, 1999

[54] CUSTOM CYLINDRICAL DIFFUSION TIPS

[75] Inventors: Daniel R. Doiron, Santa Ynez; Hugh L. Narciso, Jr., Mountain View; Christine J. Radasky, San Diego; Steven C. Anderson, Sunnyvale, all of Calif.

[73] Assignee: Miravant Systems, Inc., Santa Barbara, Calif.

[21] Appl. No.: 08/843,601

[22] Filed: Apr. 16, 1997

Related U.S. Application Data

[60] Provisional application No. 60/015,508, Apr. 16, 1996.

[51] Int. Cl.$^6$ .................................................. G02B 23/26
[52] U.S. Cl. ......................... 385/139; 385/31; 385/902
[58] Field of Search .................................. 385/15, 31, 36, 385/123, 76, 77, 139, 147, 902

[56] References Cited

U.S. PATENT DOCUMENTS

| | | | |
|---|---|---|---|
| 4,195,907 | 4/1980 | Zamja et al. | 385/147 X |
| 4,660,925 | 4/1987 | McCaughan, Jr. | 385/76 X |
| 5,147,937 | 9/1992 | Frazza et al. | 525/243 |
| 5,267,995 | 12/1993 | Doiron et al. | 385/123 X |
| 5,330,465 | 7/1994 | Doiron et al. | 385/115 |
| 5,337,381 | 8/1994 | Biswas et al. | 385/36 |
| 5,346,954 | 9/1994 | Wu et al. | 525/85 |
| 5,363,458 | 11/1994 | Pan et al. | 385/36 X |
| 5,373,571 | 12/1994 | Reid et al. | 385/36 X |

*Primary Examiner*—John D. Lee
*Attorney, Agent, or Firm*—Bryan Cave LLP

[57] ABSTRACT

A light diffuser tip for use with an optical fiber. The diffuser tip is affixed to an optical fiber and comprises an optically transparent elastomer core positioned to receive light from the output terminus of the optical fiber. The concentration of scattering centers embedded in the transparent elastomer core varies along the length of the core to yield a particular light distribution pattern. For example, the scattering centers may be distributed within an optically transparent elastomeric core material such as silicone to provide a scatterer density gradient along the diffuser tip in the axial direction of the optical fiber. A diffuser tip which provides uniform cylindrical light output intensity in air will provide a different output intensity distribution in a medium with a different index of refraction such as human tissue. The distribution of scattering centers within the transparent core of the diffuser tip can be customized to provide a substantially uniform radiance along the length of the diffuser tip when the tip is embedded within a medium having an index of refraction different from air. Such a custom diffuser tip is particularly useful for laser radiation treatment of tumors. Similarly, the concentration gradient of scatterers within the transparent core of the diffuser tip can be adjusted to provide an output light intensity distribution which will uniformly illuminate the wall of an irregular cavity.

5 Claims, 3 Drawing Sheets

P                                           D

P                                           D

CUSTOM CYLINDRICAL DIFFUSION TIPS

This application claims the benefit of U.S. Provisional Application No. 60/015,508, filed on Apr. 16, 1996.

BACKGROUND OF THE INVENTION

1. Field of the Invention

A light diffuser tip for controlling the light intensity distribution emanating from an optical fiber or fiber bundle.

2. Description of the Prior Art

An optical fiber generally consists of an optically transmissive core, a reflective cladding surrounding the core and an outer jacket which facilitates handling. There are several ways that the cylindrical diffusion of radiant energy from an optical fiber core can be accomplished. One way is to choose a ratio of the indices of refraction between the cladding and the core region of the optical fiber so that internal reflection within the core region is substantially less than total. This causes light to enter the cladding. If scattering centers are present in the cladding the light can radiate outward to emerge through the (preferably transparent) cladding.

Another way is to alter the interface between the optical fiber core and cladding to increase side radiation. Texturing the outer surface of the core region to provide a ground glass effect is one method commonly used. Another is positioning or embedding light scattering elements such as tiny particles at the surface of the optical fiber core near the interface with the cladding. Light scattering particles can also be imbedded throughout the cladding to enhance the side delivery of radiation. Combinations of these measures are also possible.

Clark, in U.S. Pat. No. 4,336,809 describes a tissue photo irradiation system for use with hematoporphyrin dyes and derivatives thereof. Clark describes the use of an optical needle which serves as a linear radiator or a cylindrical diffuser and which can be coupled to an optical fiber by means of a conventional optical coupler. Clark's needle includes a fiber optic core that is generally internally reflecting. The core is surrounded by a cladding as generally known; but in an end region a different cladding surrounds the core to make it into a radiator instead of an internally reflecting transmitter. When the cladding contains scatterers, the "needle" or diffusion tip comprises a transparent core surrounded by a scattering layer in which the concentration of scatterers is homogeneous along its length.

McCaughan, Jr., in U.S. Pat. No. 4,660,925, incorporated herein by reference, describes a cylindrical diffuser tip that overcomes some of the problems with prior art diffuser tips. McCaughan Jr. suggests (column 4, lines 48–62) providing a tip surrounding the core of an optical fiber, the tip containing a gradient of scatterers which increases logarithmically in concentration along the fiber axis in a direction toward the polished tip of the optical fiber. To accomplish this, McCaughan, Jr. teaches a method for making such a tip comprising the steps of exposing (i.e. stripping the cladding away from) the core of an optical fiber near its tip, polishing the exposed core and repeatedly dipping the tip in a curable medium containing different concentrations of scatterers to allegedly increase the concentration of scatterers along the length of the exposed core. Such a method of repetitive coating followed by the step underlined above is inoperable to produce a longitudinal gradient of scatterers in a diffuser tip. This method produces a radial gradient in scatterer concentration; the concentration of scatterers varying radially with distance from the fiber core axis. Even if this method could, by further experimentation, be made operable, such a method would provide, at best, a discrete, step-wise concentration gradient which would only approximate a logarithmic gradient in the limit of infinite coatings.

The present optical fiber cylindrical diffuser tip technology is limited in clinical applications due to an output intensity distribution which may not uniformly illuminate a target surface which makes treatment dosimetry uncertain and clinical results inconsistent.

It is desirable, therefore, to provide a cylindrical diffuser for use as a termination on an optical fiber which overcomes most or all of the limitations stated above. In particular, it is desirable to provide a cylindrical diffuser tip for an optical fiber which provides a desired intensity distribution when immersed in a medium other than air, such as human tissue, and may be further customized to uniformly illuminate a target tissue presenting an irregular geometry.

SUMMARY OF THE INVENTION

An object of this invention is to provide a diffusion tip for an optical fiber or bundle of fibers, the tip having a controlled concentration gradient of scattering centers throughout its length which enables the cylindrical diffusion of radiant energy from the fiber uniformly along the length of the tip in a medium other than air.

A further object is to provide an optical fiber or fiber bundle cylindrical diffusion tip for use in Photodynamic Therapy treatment of tumors which efficiently and uniformly cylindrically diffuses transmitted light.

Another object of this invention is to provide a diffuser tip for an optical fiber or optical fiber bundle wherein the concentration of scattering centers within the tip may be altered to provide a customized distribution of diffused light. To uniformly illuminate an irregular target surface.

The features of the invention believed to be novel are set forth with particularity in appended claims. However, the invention itself, both as to organization and method of operation, together with further objects and advantages thereof may best be understood by reference to the following description taken in conjunction with the accompanying drawings.

BRIEF DESCRIPTION OF THE FIGURES

FIG. 2b is the horizontal cursor profile of the intensity in accordance with FIG. 2a.

FIG. 3b is the horizontal cursor profile of the intensity in accordance with FIG. 3a.

FIG. 4b is the horizontal cursor profile of the intensity in accordance with FIG. 4a.

FIG. 5b is the horizontal cursor profile of the intensity in accordance with FIG. 5a.

FIG. 6b is the horizontal cursor profile of the desired diffuser tip light output intensity in accordance with the demands imposed by target geometry in FIG. 6a.

DESCRIPTION OF THE PREFERRED EMBODIMENTS

Figure 1:
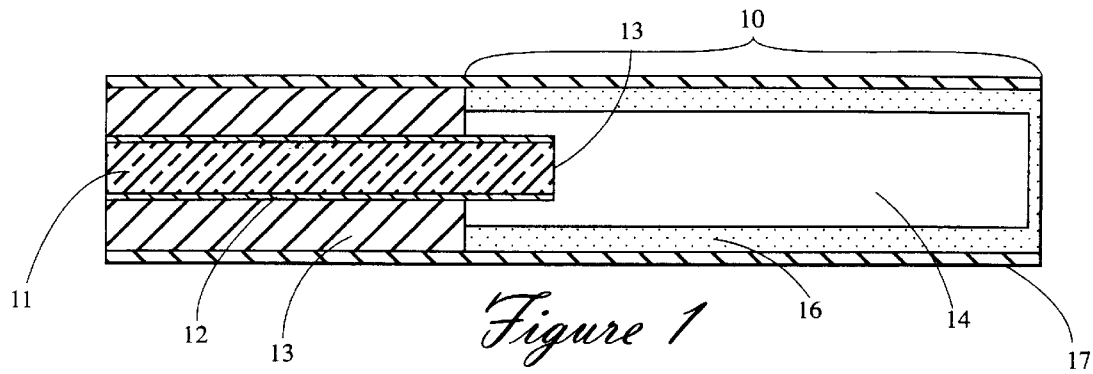
FIG. 1 is a schematic diagram of a fiber optic terminating in a cylindrical diffuse tip.

A cylindrical diffuser tip for an optical fiber is indicated generally at 10 in FIG. 1. A standard optical fiber has a blunt distal end indicated at 13. The silicone diffuser tip 10 has a proximal end which is recessed to accommodate the distal end 13 of the optical fiber core 11. In practice, the outer diameter of the silicone diffuser tip is greater than the outer diameter of the optical fiber core 11 plus cladding 15 but less than the outer diameter of the optical fiber's jacket 17. The silicone diffuser tip may be any length but is preferably between 0.5 and 5 cm for irradiation of tumors in Photodynamic Therapy.

The distribution of scattered light emanating from the silicone core of the diffuser tip can be controlled by varying the concentration gradient of scatterer in the silicone. If the concentration of scatterer is moderate and homogeneous along the length of the core of the diffuser tip, a linear intensity distribution with negative slope may result. If the concentration increases exponentially along the core the distribution of radiant energy emanating radially from the core will be linear with a zero slope as is desired. Other gradients can, of course, be used to generate other desired distributions of light.

A diffusion tip having a continuous gradient of scattering centers embedded in an-optically transparent extrudable material such as silicone elastomer is described by Doiron, et al. in U.S. Pat. No. 5,196,005. The optically transparent core of the difuser tip is conveniently made by extrusion. Extrusion processes for forming cylindrical articles are well known in the art. To produce an elastomeric core for the diffuser tip which has the desired concentration gradient of light scatterers embedded therein, a dual injector system (or multiple injector system) is employed. A first injector contains a mixture of highly concentrated scatterers in the elastomer base. A second injector contains a low concentration of scatterers in elastomer or elastomer alone. The two mixtures are forced through check values by pumps and into a mixer where they are combined in volumes predetermined to produce the desired final concentration of scatterers in the diffuse tip core which emerges from the extruder through one or more orifices of an extrusion die.

While the dual injection and mixing processes are occurring, an on-line detection system monitors the concentration of light scatterers in the core as the core is extruded. This information is relayed to a controller system (not shown) which regulates the flow from each injector to produce the optimum concentration gradient. Once determined, this optimum concentration gradient can be reproduced by programming the appropriate algorithms into a controller which independently regulates the injectors. The extruded core comprising an extrudable transparent elastomer with the desired concentration gradient of scattering centers embedded therein is cured and forced into a plastic tube, the inner diameter of the tube being equal to or greater than the outer diameter of the optical fiber to which the tip is to be attached.

Figure 2A:
FIG. 2a shows the light output intensity distribution of a diffuser tip showing the relatively uniform intensity distribution in air.
Figure 2B:
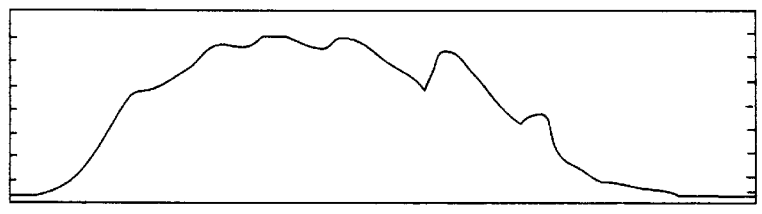
Figure 3A:
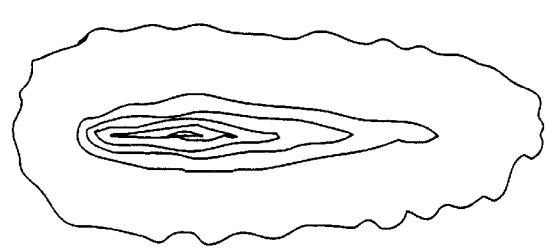
FIG. 3a shows the output distribution of the same fiber when submersed in water having an index of refraction of 1.33.
Figure 3B:
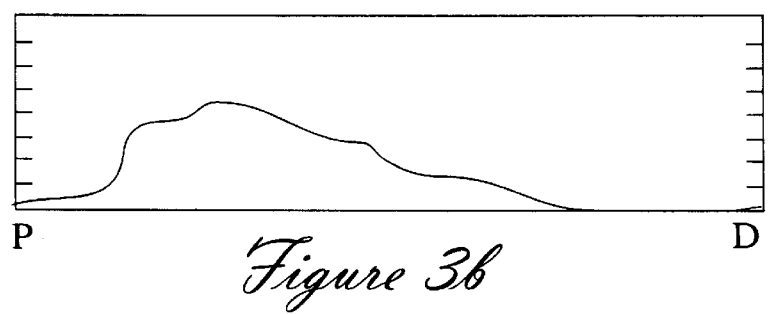

The output light intensity distribution of a cylindrical diffuser tip is described in U.S. Pat. No. 5,196,005 and is shown in FIGS. 2a and 2b. The light intensity output distribution shown in FIGS. 2a and 2b was recorded in air. The light intensity output in FIGS. 2a and 2b is relatively uniform with mean deviation of 21% for the diffusing portion of the tip. FIG. 3 shows the light output intensity distribution of the same diffuser tip when submersed in water having an index of refraction of 1.33 which index nire nearly approximates the index of refraction of tissue which is ≅0.4. The output distribution pattern is significantly shifted toward the start or proximal end the diffusing tip. This is also indicated by the percent mean deviation increasing to 59% compared to the distribution in air. Such a shift in light intensity distribution could significantly alter the light induced therapeutic response along diffuser tip and therefore greatly affect the overall clinical response. Such diffusing tips terminus on fibers have been tested in photodynamic therapy of the prostate, and there is an in vivo shift in the output light intensity distribution in tissue with respect to the air.

Figure 4A:
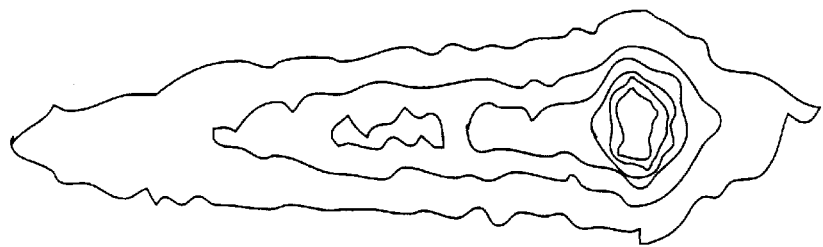
FIG. 4a shows the output distribution of a fiber optic diffuser tip in air in which the scattering centers are distributed having decreased concentration from left to right.
Figure 4B:
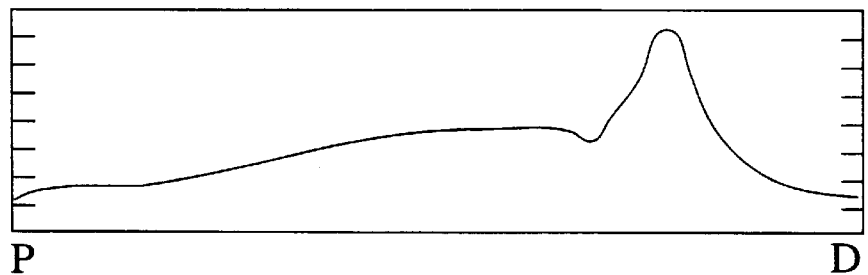
Figure 5A:
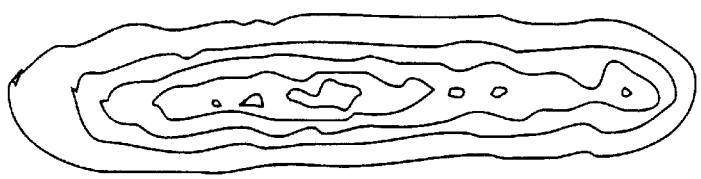
FIG. 5a shows the same diffuser tip output as in FIG. 3 when the tip is submerged in water having an index of refraction of 1.33.
Figure 5B:
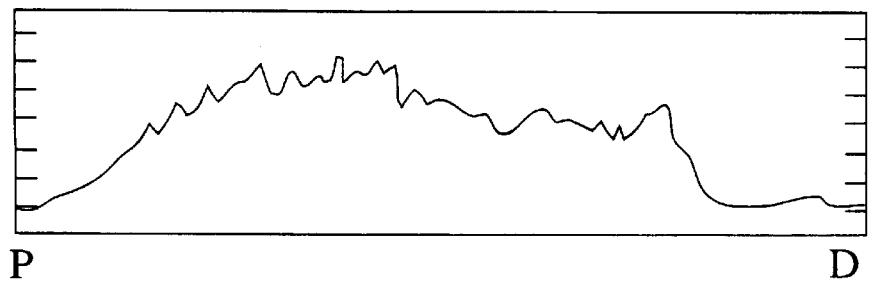

An example of such customizing in shown in FIGS. 4a and 4b, and in FIGS. 5a and 5b. In FIG. 4a, the output distribution of a diffuser tip in air is shown in which the scattering centers distribution within the diffuser tip have decreased along the length of the tip in the proximal direction and increased in the distal direction relative to the where the concentration would be if the diffuser tip was to be used in an air medium. This shifts the output distribution to a non-uniform pattern with less output at the proximal end and more at the distal end. This shift would make such a diffuser tip non-optimal for clinical applications. FIG. 5a shows the same diffuser tip as FIG. 4a, but submersed in water. The output distribution has now shifted toward a more uniform pattern that is ideal for the diffuser since it now uniformly delivers a cylindrical pattern of light along the complete length of the diffuser tip. FIGS. 2b, 3b, 4b and 5b show the profile of light output intensity along the length of the respective tips corresponding thereto.

Figure 6A:
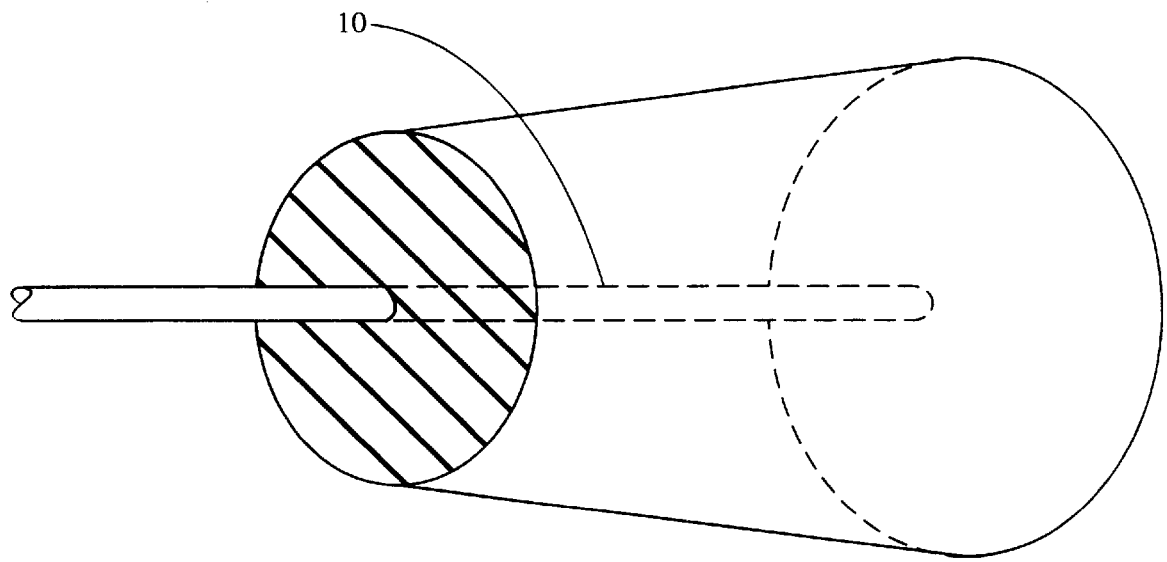
FIG. 6a is a schematic diagram showing a light diffuser tip positioned within a tapered cavity.
Figure 6B:
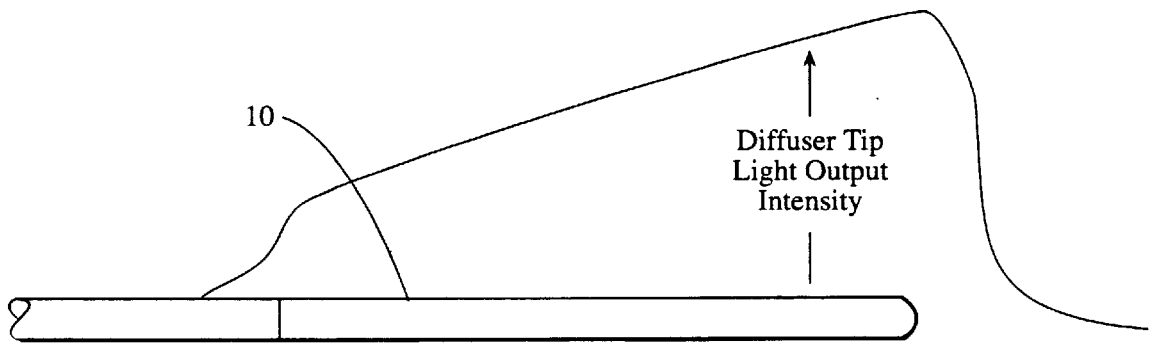

The scattering center distribution within a transparent diffuser tip core can also be used to give controlled, non-uniform output distribution from a cylindrical diffuser in a given medium of known index of refraction. For instance, in the illumination of a known uniform mass or cavity where the cavity is smaller at one end than the other as shown, for example, in FIG. 6a. The output illumination at the base of the diffuser tip should be lower at the proximal end of the diffuser tip 10 where the area of the cavity to be illuminated is relatively less, while at the distal end of the diffuser tip, a greater illumination is desired due to the relatively greater cavity surface or area requiring illumination. FIG. 6b shows the output of a diffuser tip designed to provide a light intensity output distribution along its length in accordance with the demands imposed by the shape of the cavity shown in FIG. 6a.

In addition to adjusting the diffuser tip output light to conform to a particular cavity shape, the scattering center concentration distribution pattern within the customized diffusing tip must also be chosen to take into account the index of refraction of the medium the diffuser tip will be immersed in. The particular concentration distribution of scattering centers within a tip will depend upon the application and can be empirically determined. One method is to construct a "modular" diffuser tip from a plurality of core plugs, each plug having a particular concentration of scatterers therein. A prototype tip is constructed by placing plugs end to end. The plugs are interchanged and manipulated until the diffuser tip's light output intensity curve has the desired shape. The plug sequence can be used to control the concentration of scatterers mixed with elastomer during extrusion to provide a unitary tip having output characteristics approximating the output of the modular prototype tip.

While particular embodiments of the present invention have been illustrated and described, it would obvious to those skilled in the art that various other changes and modifications can be made without departing from the spirit and scope of the invention. For example, the concentration of light scattering particles or "centers" within the optically transparent core can be varied to produce a diffuser light intensity output pattern having almost any desired distribution pattern. Thus, tips may be designed for delivering uniform illumination to the inner wall of an irregularly shaped cavity. It is therefore intended to cover in the appended claims all such changes and modifications that are within the scope of this invention.

What we claim is:

1. A light diffuser tip for illuminating a medium having one or more indices of refraction associated therewith, the diffuser tip having a proximal end which is adjacent to the tip of an optical waveguide and a distal end and a length therebetween, the diffuser tip comprising a substantially transparent cylindrical center core containing a plurality of optical scatterers distributed therein, the distribution and concentration of the scatterers being based upon the indices of refraction of the medium so that a desired light intensity distribution is provided along the length of the diffuser tip when illuminating the medium.

2. The device of claim 1 wherein the diffuser tip is adapted to deliver light conducted through at least one optical fiber.

3. The device of claim 1 wherein the medium is human tissue.

4. The device of claim 1 wherein the distribution and concentration of the optical scatterers is based upon the indices of refraction of the medium so that a substantially uniform light intensity distribution is provided along the entire length of the diffuser tip when illuminating the medium.

5. The device of claim 1 wherein the distribution and concentration of the optical scatterers is based upon the indices of refraction of the medium so that a predetermined non-uniform light intensity distribution is provided along the entire length of the diffuser tip when illuminating the medium.

* * * * *